(12) United States Patent
Naik et al.

(10) Patent No.: US 9,851,472 B2
(45) Date of Patent: Dec. 26, 2017

(54) SILICONE-BASED HYDROPHILIC COPOLYMER AND HYDROGEL COMPOSITIONS COMPRISING THE SAME

(71) Applicants: Sandeep Naik, Bangalore (IN); Shreedhar Bhat, Bangalore (IN); Chetan Shah, Bangalore (IN); Anubhav Saxena, Bangalore (IN); Raveendra Mathad, Bangalore (IN)

(72) Inventors: Sandeep Naik, Bangalore (IN); Shreedhar Bhat, Bangalore (IN); Chetan Shah, Bangalore (IN); Anubhav Saxena, Bangalore (IN); Raveendra Mathad, Bangalore (IN)

(73) Assignee: MOMENTIVE PERFORMANCE MATERIALS INC., Waterford, NY (US)

( * ) Notice: Subject to any disclaimer, the term of this patent is extended or adjusted under 35 U.S.C. 154(b) by 0 days.

(21) Appl. No.: 14/670,557

(22) Filed: Mar. 27, 2015

(65) Prior Publication Data

US 2016/0282517 A1 Sep. 29, 2016

(51) Int. Cl.
| | |
|---|---|
| *G02B 1/04* | (2006.01) |
| *C08F 230/08* | (2006.01) |
| *A61K 8/90* | (2006.01) |
| *A61Q 19/00* | (2006.01) |
| *C08L 43/04* | (2006.01) |

(52) U.S. Cl.
CPC ............. *G02B 1/043* (2013.01); *A61K 8/90* (2013.01); *A61Q 19/00* (2013.01); *C08F 230/08* (2013.01); *C08L 43/04* (2013.01)

(58) Field of Classification Search
CPC ............................. C08F 30/08; C08F 230/08
USPC ........................................................ 526/279
See application file for complete search history.

(56) References Cited

U.S. PATENT DOCUMENTS

| | | | |
|---|---|---|---|
| 3,408,429 A | 10/1968 | Otto | |
| 3,496,254 A | 2/1970 | Wichterle | |
| 4,084,459 A | 4/1978 | Clark | |
| 4,197,266 A | 4/1980 | Clark et al. | |
| 4,260,725 A | 4/1981 | Keogh et al. | |
| 5,079,139 A * | 1/1992 | Bolger | C09B 23/0075 430/510 |
| 5,352,714 A | 10/1994 | Lai et al. | |
| 5,981,669 A | 11/1999 | Valint et al. | |
| 5,998,498 A | 12/1999 | Vanderlaan et al. | |
| 6,013,711 A | 1/2000 | Lewis et al. | |
| 6,207,782 B1 | 3/2001 | Czech et al. | |
| 6,867,245 B2 | 3/2005 | Iwata et al. | |
| 7,550,519 B2 * | 6/2009 | Phelan | B29D 11/00903 523/105 |
| 7,557,231 B2 | 7/2009 | Schorzman et al. | |
| 7,601,766 B2 | 10/2009 | Schorzman et al. | |
| 7,732,546 B2 | 6/2010 | Salamone et al. | |
| 7,781,558 B2 | 8/2010 | Schorzman et al. | |
| 7,825,273 B2 | 11/2010 | Schorzman et al. | |
| 8,557,940 B2 * | 10/2013 | Chang | C08G 77/388 351/159.02 |
| 8,642,712 B2 | 2/2014 | Chang et al. | |
| 2006/0055882 A1 * | 3/2006 | Phelan | B29D 11/00317 351/159.28 |
| 2008/0231798 A1 | 9/2008 | Zhou et al. | |
| 2009/0005528 A1 * | 1/2009 | Fujisawa | C07F 7/0854 526/279 |
| 2009/0143499 A1 | 6/2009 | Chang et al. | |
| 2010/0296049 A1 | 11/2010 | Justynska et al. | |
| 2010/0298446 A1 | 11/2010 | Chang et al. | |
| 2011/0166248 A1 | 7/2011 | Hsu et al. | |
| 2013/0172600 A1 | 7/2013 | Chang et al. | |
| 2014/0235782 A1 | 8/2014 | Fujisawa et al. | |
| 2015/0011788 A1 | 1/2015 | Saxena et al. | |

OTHER PUBLICATIONS

International Search Report and Written Opinion of the International Searching Authority, PCT/US2016/023923, Momentive Performance Materials, Inc., dated Jun. 23, 2016.

* cited by examiner

*Primary Examiner* — Marc Zimmer
(74) *Attorney, Agent, or Firm* — Joseph Ostroff; McDonald Hopkins LLC

(57) ABSTRACT

A hydrophilic siloxane copolymer of siloxane and hydrophilic organic monomer/s The copolymers can be functionalized to make them capable of undergoing further polymerization by thermal or actinic radiations. The hydrophilicity of these polymers can be varied by varying the siloxane versus organic monomer ratio thereby going from water dispersible to soluble states. The siloxane content can be tuned accordingly in order to provide moderate to high oxygen permeability. These copolymers can be used as a single component curable composition which results in hydrogels to minimize the presence of leachable components thus by reducing the processing cost. The polymers may also find applications in personal care formulations as copolymers, film-formers, hydrogels, coating, emulsions/latex etc.

18 Claims, No Drawings

SILICONE-BASED HYDROPHILIC COPOLYMER AND HYDROGEL COMPOSITIONS COMPRISING THE SAME

FIELD

The present invention relates to copolymers exhibiting hydrophilic properties. In particular, the present invention relates to copolymers of organo-modified siloxanes and organic monomers that exhibit hydrophilic properties. The copolymers may be used to form hydrogel compositions suitable for making hydrogel films suitable for use in various products including, but not limited to, biomedical products such as contact lenses.

BACKGROUND

Reactive silicone containing hydrogel formulations are used to make extended wear soft contact lens as silicone imparts high oxygen permeability, flexibility leading to comfort and reduced corneal complications. But these siloxane molecules lack inherent wettability and thereby a compromise is made between oxygen permeability and water uptake. Traditionally these siloxane monomers are blended with organic hydrophilic monomers to prepare curable monomer mixture which can be actinically or thermally cured. However, mixing siloxane and organic monomers lead to incompatibility causing macro-phase separation and development of opacity. A possible solution to this problem is to modify the siloxane monomers with organic moiety which restricts the phase separation to the micro-level increasing its compatibility in the curable mixture and brings in some inherent hydrophilicity. These organo-modified siloxane monomers are cured along with organic monomers in presence of cross-linkers.

Examples of prior attempts of such methodology include those described in U.S. Pat. Nos. 4,260,725; 5,352,714; 5,998,498; 6,867,245; 6,013,711; 6,207,782; 7,601,766; 7,557,231; 7,732,546; 7,781,558; 7,825,273. But this approach leads to a large number of unreacted monomers due to mismatch in the reactivity ratio of the monomers involved. Further, this method leads to uncontrolled cross-linking and molecular weight build-up, which affects the batch to batch reproducibility. Since there are multiple components involved in the formulation, the chances of having unreacted monomers are high and hence it is necessary to extract these leachable monomers from the matrix, such as by aqueous-organic solvent mixtures, which leads to increased processing costs.

U.S. Pat. No. 5,981,669 discloses the synthesis of a mono-functional pre-polymer by free radical polymerization of a silicone monomer and a hydrophilic monomer in the presence of a chain transfer agent. These pre-polymers were then introduced into formulations with bi-functional macromers, which may be composed of silicone. U.S. Patent Publication Nos. 2011/0166248 and 2008/0231798 discloses block copolymers of silicone containing monomers with hydrophilic monomers to yield a pre-polymer. U.S. Patent Publication No. 2010/0298446 and U.S. Pat. No. 8,642,712 report functionalization of polysiloxane blocks to act as a macro initiator for polymerizing a hydrophilic monomer via ATRP. This technique yields bi or tetra functional pre-polymers. U.S. Patent Publication No. 2010/0296049 and U.S. Pat. No. 8,557,940 discloses RAFT technique for polymerizing a mixture of bi-functional polysiloxane polymer and organic monomer. U.S. Patent Publication No. 2009/0143499 covers a pre-polymer made of polysiloxane blocks, poly(oxyalkylene) blocks, and cross-linkable groups. U.S. Patent Publication No. 2014/0235782 discloses pre-polymer based on homo-polymerization of hydrophilic monomers. U.S. Patent Publication No. 2013/0172600 discloses pre-polymer approach wherein the polysiloxane units are used as a cross-linker to prepare the polymer and functionalization of the same. U.S. Pat. No. 7,550,519 discloses the FRP method to produce colored hydrogel lenses from reactive polymers.

SUMMARY

This invention provides a linear copolymer of siloxane and hydrophilic organic monomer/s via free radical polymerization (FRP) or atom transfer radical polymerization (ATRP). These copolymers can be functionalized further in variable amounts to make them capable of undergoing further polymerization by thermal or actinic radiations. The hydrophilicity of these polymers can be varied by varying the siloxane versus organic monomer ratio thereby going from water dispersible to soluble states. The siloxane content can be tuned accordingly in order to get moderate to high oxygen permeability. These pre-polymers can be used as a single component curable composition which results in hydrogels to minimize the presence of leachable components thus by reducing the processing cost. They may also find applications in personal care formulations as copolymers, film-formers, hydrogels, coating, emulsions/latex etc.

In one aspect, the present invention provides a pre-polymer approach to synthesize organosilicone polymers comprising copolymerizing monomers and purifying the polymers for any low molecular weight reactive or unreactive species. These polymers are functionalized further into a reactive species termed as a pre-polymer. These pre-polymers can be cured in the neat form or with any additional component to yield hydrogel films which require minimum amount of post-processing steps. These pre-polymers can be tuned for hydrophilicity and/or oxygen permeability by right selection of monomer with optimum ratio. This approach brings in reproducibility and increases the purity of the final materials.

In one aspect, the present invention provides a hydrophilic siloxane copolymer of the formula (1):

$$[W]_l[A]_m[B]_n[C]_p \quad (1)$$

wherein l is 1, m and n are independently 1-200, and $2 \leq l+p \leq 200$;

W is a moiety having the general formula (2):

$$D-E---- \quad (2)$$

wherein E is a divalent moiety chosen from substituted, un-substituted, aliphatic, aromatic, cyclic, or acyclic hydrocarbon radical having 1-20 carbon atoms, optionally containing sulfur or oxygen; D is a monovalent hydrocarbon radical with 1-10 carbon atoms with a functional group independently selected from a hydroxy, an ether, an ester, an amine, an amide, a carboxylic acid, or a combination of two or more thereof;

A is an organosilicone block having the general formula (3):

wherein $R_1$, $R_2$, and $R_3$ are independently selected from hydrogen or a monovalent hydrocarbon radical with 1 to 10 carbon atoms optionally containing heteroatoms; and F is a siloxane-containing group;

B is a hydrophilic block having the general formula (13)

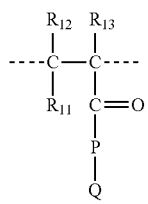

(13)

wherein P is selected from O or $NR_{14}$ wherein $R_{14}$ is a hydrogen or monovalent hydrocarbon radical with 1 to 5 carbon atoms optionally containing a heteroatom; $R_{11}$, $R_{12}$, and $R_{13}$ are independently selected from a hydrogen or monovalent hydrocarbon radical with 1 to 10 carbon atoms optionally containing a heteroatom; Q is a substituted or un-substituted, aliphatic, aromatic, cyclic, or acyclic hydrocarbon radical comprising of 1-50 carbon atoms, optionally containing a heteroatom, with a functional group independently selected from a hydroxyl, an ether, an ester, an amine, or a carboxylic acid; and C is an organic block having the general formula (14)

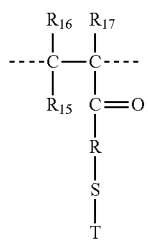

(14)

wherein $R_{15}$, $R_{16}$, and $R_{17}$ are independently selected from a hydrogen or monovalent hydrocarbon radical with 1-10 carbon atoms; R is selected from O or $NR_{18}$ wherein $R_{18}$ is hydrogen or a monovalent hydrocarbon radical with 1 to 5 carbon atoms optionally containing a heteroatom; S is a divalent hydrocarbon radical with 1-20 carbon atoms chosen from a substituted or un-substituted aliphatic, cyclic, or aromatic hydrocarbons, optionally containing a heteroatom; and T is a monovalent hydrocarbon radical with 1-10 carbon atoms with a functional moiety chosen from a hydroxyl, an epoxy, an ether, an ester, an amine, an amide, or a carboxylic acid.

In one aspect, the present invention provides a composition comprising such polymers. In one embodiment, the composition is a hydrogel composition. In one embodiment, the composition is an emulsion or a latex. In one embodiment the composition is a film-former.

In one embodiment, the present invention provides an article comprising such compositions. In one embodiment, the article is a contact lens formed from a hydrogel film produced from the compositions. In one embodiment, the article comprises a substrate having a surface where the surface is at least partially coated with the composition.

DETAILED DESCRIPTION

The present invention provides polymer materials that exhibit hydrophilic properties. The polymer materials may be used in a variety of compositions including, for example, emulsions, coatings, film-former, hydrogel compositions for making films, etc. The compositions can be used in a variety of applications including in biomedical applications as a coating or to form part or all of a desired product, e.g., in contact lenses. The present polymers have been found to be suitable for forming films exhibiting hydrophilic properties while reducing the concentration of leachable monomers that may be present in conventional hydrogel compositions.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

The terms "radical" and "group", as applied to the terms "alkyl," "cycloalkyl," "aryl," "alkoxy," "aryloxy," and "cycloalkoxy" are used interchangeably throughout the disclosure.

Throughout the disclosure, the term "hydrocarbon radical" represents any of an aliphatic radical, a cycloaliphatic radical, or an aromatic radical having from one to sixty carbon atoms. The following general definitions for "aliphatic," "cycloaliphatic," and "aromatic" radicals are applicable for monovalent and divalent "hydrocarbon radicals."

The term "aliphatic" radical or group refers to an array of carbon atoms that is not cyclic, with the point(s) of attachment being an $sp^3$ carbon atom. The array of carbon atoms may further comprise any combination of $sp^3$, $sp^2$, or sp hybridized carbon atoms. The array of carbon atoms may further comprise one or more heteroatoms, such as oxygen, nitrogen, and sulfur. Examples of aliphatic radicals include, but are not limited to, methyl, ethyl, n-propyl, isopropyl, n-butyl, tert-butyl, isooctyl, benzyl, cyclohexylmethyl, phenethyl, alpha, alpha-dimethylbenzyl, 3-hydroxypropyl, and the like.

The term "aromatic" radical or group refers to a monovalent cyclic array of $sp^2$ hybridized carbon atoms and conjugated carbon-carbon double bonds, and is attached via an $sp^2$ hybridized carbon atom. The aromatic group or radical can have from one to the maximum permissible number of substituents. Substituents are generally defined as radicals other than a hydrogen atom. Thus an aromatic carbon atom that is not explicitly substituted by a substituent is presumed substituted by a hydrogen atom. In one embodiment, an aromatic radical may be chosen from a C6-C20 aromatic radical; a C6-C15 aromatic radical; even a C6-C10 aromatic radical. The aromatic radical or group can further comprise heteroatoms, such as sulfur, oxygen, and nitrogen. Examples of aryl groups include phenyl, substituted, but are not limited to, phenyl, tolyl, substituted tolyl, xylyl, mesityl, chlorophenyl, naphthyl, furyl, furylmethyl, thienyl, pyrrolyl, and the like.

The term "cycloaliphatic" radical or group refers to a monovalent cyclic array of carbon atoms, and is attached to the silicon atom via an $sp^3$ hybridized carbon atom that forms part of the cyclic array of carbon atoms. The cyclic array of carbon atoms may further comprise one or more heteroatoms, such as oxygen, sulfur, and nitrogen. Further, the cyclic array of carbon atoms can be substituted with one to the maximum permissible number of substituents. Examples of cycloalkyl groups include, but are not limited to, cyclohexyl, methylcyclohexyl, trimethylcyclohexyl, phenylcyclohexyl, tetrahydropyranyl, 4-thiacyclohexyl, cyclooctyl, and the like.

A "heteroatom" includes a non-carbon atom such as, for example, nitrogen, sulfur, oxygen, etc.

A "hydrophilic" substance (e.g., hydrophilic monomer, hydrophilic macromer, hydrophilic polymer, etc.) is one that is water-loving, has an affinity for water, is capable of absorbing water, etc. A hydrophilic substance may be soluble or insoluble (e.g., substantially insoluble) in water. A hydrophilic substance can, in one embodiment, contain both hydrophilic and hydrophobic potions, but the hydrophobic portions are present in relative amounts such that the substance or component is hydrophilic. In one embodiment, a hydrophilic substance can absorb at least 10 percent by weight water.

In one aspect, the present invention provides a hydrophilic siloxane copolymer of the formula (1):

 (1)

wherein l is 1, m and n are independently 1-200, and $2 \leq l+p \leq 200$;

W is a moiety having the general formula (2):

D-E----- (2)

wherein E is a divalent moiety chosen from a substituted, un-substituted, aliphatic, aromatic, cyclic, or acyclic hydrocarbon radical having 1-20 carbon atoms, optionally containing sulfur or oxygen; D is a monovalent hydrocarbon radical with 1-10 carbon atoms with a functional group independently selected from a hydroxy, an ether, an ester, an amine, an amide, a carboxylic acid, or a combination of two or more thereof;

A is an organosilicone block having the general formula (3):

 (3)

wherein $R_1$, $R_2$, and $R_3$ are independently selected from hydrogen or a monovalent hydrocarbon radical with 1 to 10 carbon atoms optionally containing a heteroatom; and F is a siloxane-containing group;

B is a hydrophilic block having the general formula (13)

 (13)

wherein P is selected from O or $NR_{14}$ wherein $R_{14}$ is a hydrogen or monovalent hydrocarbon radical with 1 to 5 carbon atoms optionally containing a heteroatom; $R_{11}$, $R_{12}$, and $R_{13}$ are independently selected from a hydrogen or monovalent hydrocarbon radical with 1 to 10 carbon atoms optionally containing a heteroatom; Q is a substituted or un-substituted, aliphatic, aromatic, cyclic, or acyclic hydrocarbon radical comprising of 1-50 carbon atoms, optionally containing a heteroatom, with a functional group independently selected from a hydroxyl, an ether, an ester, an amino, or a carboxylic acid; and C is an organic block having the general formula (14)

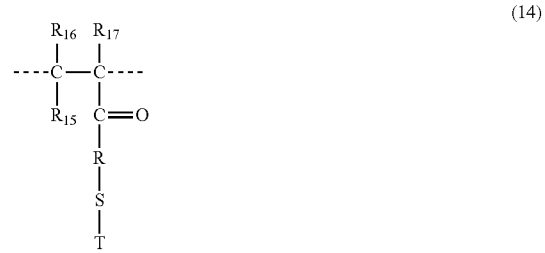 (14)

wherein $R_{15}$, $R_{16}$, and $R_{17}$ are independently selected from a hydrogen or monovalent hydrocarbon radical with 1-10 carbon atoms; R is selected from O or $NR_{18}$ wherein $R_{18}$ is hydrogen or a monovalent hydrocarbon radical with 1 to 5 carbon atoms optionally containing a heteroatom; S is a divalent hydrocarbon radical with 1-20 carbon atoms chosen from a substituted or un-substituted aliphatic, cyclic, or aromatic hydrocarbons, optionally containing a heteroatom; and T is a monovalent hydrocarbon radical with 1-10 carbon atoms with a functional moiety chosen from a hydroxyl, an epoxy, an ether, an ester, an amine, an amide, or a carboxylic acid.

The siloxane-containing component F in component A may be chosen as desired and generally comprises a group comprising at least one —O—Si linkage. Examples of suitable siloxane-containing groups for component F include, but are not limited to:

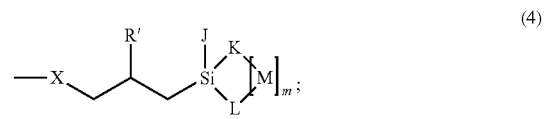 (4)

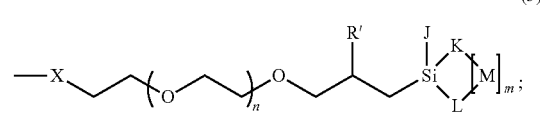 (5)

-continued

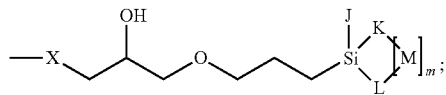  (6)

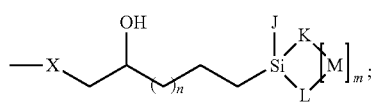  (7)

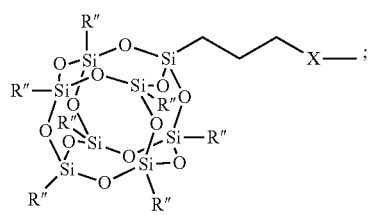  (8)

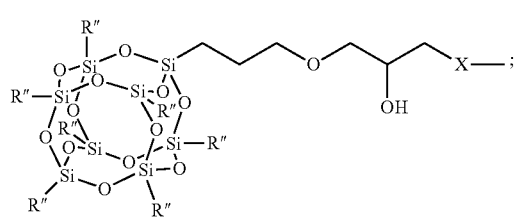  (9)

wherein R' is independently chosen from H or $CH_3$; R" is independently chosen from a hydrocarbon radical with 1-20 carbon atoms chosen from a substituted or un-substituted aliphatic, cyclic, or aromatic hydrocarbon, which may contain a heteroatom; m is an integer from 0-1; X is a functional group independently chosen from an ester or an amide; K is independently selected from $CH_3$, $—O—[Si(CH_3)_2O]n-Si(CH_3)_3$, $—OSi(CH_3)_3$

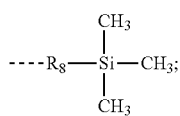  (10)

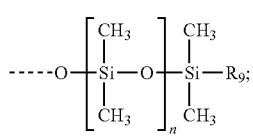  (11)

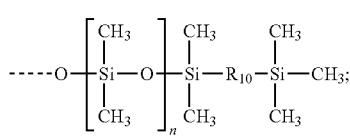  (12)

wherein $R_8$ and $R_{10}$ are selected from hydrogen or monovalent hydrocarbon radical with 1 to 5 carbon atoms and $R_9$ is selected from hydrogen or monovalent hydrocarbon radical with 1 to 10 carbon atoms; and n is an integer selected from 1-50. J and L are independently chosen from $CH_3$, $—OSi(CH_3)_3$, $—O—[Si(CH_3)_2O]n-Si(CH_3)_3$ when m is 0. When m is greater than 0, J is $CH_3$, K is $—O—Si(CH_3)_2—$; L is $—OSi(CH_3)_2O—$; and M is $—[OSi(CH_3)_2]_n—$.

In one embodiment, the organosilicone block A has the structure

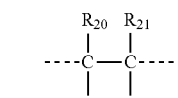  (15)

wherein $R_{19}$, $R_{20}$, and $R_{21}$ are independently selected from a hydrogen or monovalent hydrocarbon radical with 1 to 10 carbon atoms optionally contain heteroatoms; and F is expressed as having the general structure of (16):

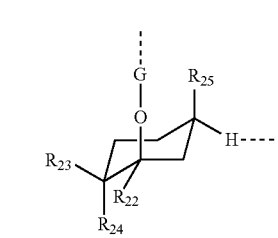  (16)

wherein $R_{22}$, $R_{24}$, and $R_{25}$ are independently chosen from a hydrogen or monovalent hydrocarbon radical with 1 to 5 carbon atoms optionally containing a heteroatom; $R_{23}$ is independently selected from functional groups such as a hydroxyl and its alkali metal salts, an alkoxy, and a halogen; G is a divalent moiety independently chosen from a substituted or un-substituted, aliphatic or aromatic, cyclic or acyclic hydrocarbon radical having 1-20 carbon atoms optionally containing a heteroatom; H is defined by the general formula (17),

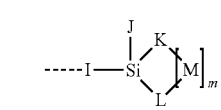  (17)

wherein I is an alkylene group with 1-16 carbon atoms; J and L are independently selected from $CH_3$, $—OSi(CH_3)_3$, $—O—[Si(CH_3)_2O]n-Si(CH_3)_3$ when m is 0; K is independently selected from $CH_3$, $—O—[Si(CH_3)_2O]n-Si(CH_3)_3$, $—OSi(CH_3)_3$

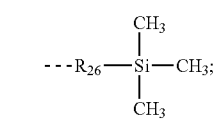  (18)

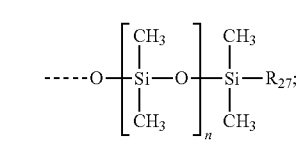  (19)

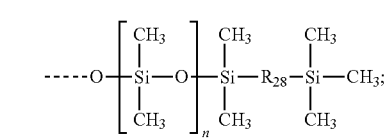  (20)

wherein $R_{26}$ and $R_{28}$ are independently chosen from a hydrogen or monovalent hydrocarbon radical with 1 to 5 carbon atoms, and $R_{27}$ is chosen from a hydrogen or monovalent hydrocarbon radical with 1 to 10 carbon atoms; and n is an integer selected from 1-50. When m is greater than 0, J is $CH_3$, K is $-O-Si(CH_3)_2-$, L is $-OSi(CH_3)_2O$, and M is $-[OSi(CH_3)_2]_n-$.

In one embodiment, H is of the formula:

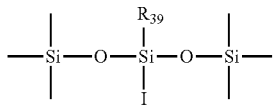

wherein $R_{39}$ is a methyl group or $-O-Si(CH_3)_3$. In another embodiment, H is of the formula:

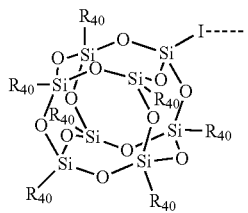

wherein $R_{40}$ is a monovalent hydrocarbon radical, linear or branched with 1-50 carbon atoms.

In an embodiment, D and T are independently selected from $OR_{29}$, $NR_{30}R_{31}$, or $-CR_{32}CR_{33}R_{34}O$, wherein $R_{29}$, $R_{30}$, $R_{31}$, $R_{32}$, $R_{33}$, and $R_{34}$ are independently selected from hydrogen or a monovalent hydrocarbon radical with 1 to 5 carbon atoms. In an embodiment, D and at least one T in a compound of Formula (1) is selected as U, which has the general formula (21), and U≥2:

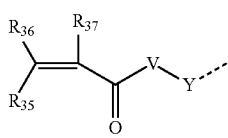

(21)

where V is selected from $-O-$ or $NR_{38}$, wherein $R_{35}$, $R_{36}$, $R_{37}$, and $R_{38}$ are independently chosen from a hydrogen or monovalent hydrocarbon radical with 1 to 5 carbon atoms; and Y is chosen from a divalent substituted or un-substituted, aliphatic hydrocarbon radical with 1-10 carbon atoms optionally containing a heteroatom.

The properties of the polymer and compositions formed by the polymer may be controlled or tuned by varying the ratio of the various blocks (i.e., the monomers) in the polymer. In one embodiment, the ratio of the m:n:p units is from about 5-60:20-80:5-60; from about 10-50:25-75:10:50; from about 15-40:30-60:15-40; even from about 20-30:40-50:20-30, with the proviso that the ratio adds up to 100. Here as elsewhere in the specification and claims, numerical values may be combined to form new and non-disclosed ranges.

The present invention also provides compositions comprising the polymers in accordance with Formula (1). In an embodiment, the polymers may be used as part of a hydrogel composition. A hydrogel composition may comprise (a) a polymer of Formula (1); (b) a cure initiator; (c) optionally a polymerizable monomer; and (d) optionally a cross-linking agent. The present polymers can be used as a single component curable composition, that is, additional, conventional, co-monomers (c) are not required.

The cure initiator (b), for example, can be selected from materials known for such use in the polymerization art in order to promote and/or increase the rate of the polymerization reaction. An initiator is a chemical agent capable of initiating polymerization reactions. The initiator can be a photo-initiator or a thermal initiator.

A photo-initiator can initiate free radical polymerization and/or cross-linking by the use of light. Suitable photo-initiators include, but are not limited to, benzoin methyl ether, diethoxyacetophenone, benzoylphosphine oxide, 2-hydroxy-2-methyl propiophenone (HMPP), 1-hydroxycyclohexyl phenyl ketone and Darocur and Irgacure types, preferably Darocur® 1173 and 2959. Examples of benzoylphosphine initiators include 2,4,6-trimethylbenzoyldiphenylphosphine oxide; bis-(2,6-dichlorobenzoyl)-4-N-propylphenylphosphine oxide; and bis-(2,6-dichlorobenzoyl)-4-N-butylphenylphosphine oxide. Reactive photo-initiators that can be incorporated, for example, into a macromer or can be used as a special monomer are also suitable. Examples of reactive photo-initiators include those disclosed in EP 632329, which is herein incorporated by reference in its entirety. The polymerization can then be triggered off by actinic radiation, for example light, in particular UV light of a suitable wavelength. The spectral requirements can be controlled accordingly, if appropriate, by addition of suitable photosensitizers.

Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator are azobisisobutyronite (AIBN) and 1,1'-Azobis(cyclohexanecarbonitrile).

RAFT refers to reversible addition fragmentation chain transfer technique used in the polymerization. RAFT Reagent refers to a compound having the general formula, $K-C(S)-S-R^{39}$ in which $R^{39}$ is a leaving group and K is an activating group. The terms used here have its traditional meanings as understood by skilled persons in the art. Any known RAFT reagents can be used in the invention for synthesizing pre-polymers, RAFT reagents belong to dithiobenzoates, trithiocarbonates, xanthates, and dithiocarbamates classes are considered in the RAFT reactions. The preferred reagent is 4-cyano-4-(phenylcarbonothioyltrio) pentanoic acid and 2-(Dodecylthiocarbonothioylthio)-2-methylpropionic acid in the context of present invention.

ATRP refers to atom transfer radical polymerization techniques, well known in the art, used in living radical polymerization. ATRP conditions involve the utilization of an initiator and a catalyst. ATRP initiators can be selected from any of the following class, halogenated alkanes, benzylic halides, alpha-haloesters, alpha-haloketone, alpha-halonitrile, or sulfonyl chloride. The ATRP catalyst is a metal ligand complex with metal part comprising of Mo, Cr, Re, Ru, Fe, Rh, Ni, Pd, Cu and a ligand. The ligand used can be a bidentate (e.g., 2,2'-bipyridine, N,N,N',N'-tetramethyl ethylenediamine), tridentate (e.g., N,N,N',N'',N''-pentamethyldiethylenetriamine (PMDETA)), or tetradentate (e.g., 1,1,4,7,10,10-hexamethyltriethylenetetramine, tris(2-(dimethylamino)ethyl)amine)). A suitable catalyst is Cu-PMDETA complex.

The composition optionally comprises a polymerizable monomer (c). Generally, hydrogels comprise a polymer, e.g., a hydrophilic polymer or monomer, and a co-monomer, e.g., a methacrylate, N-vinylpyrrolidone, methacrylic acid, etc. In the present compositions, however, such monomers are not required, and a hydrogel may be formed by direct curing of the polymer (a). In conventional hydrogel films, the co-monomers are typically employed in concentrations of about 30 to about 40 percent by weight of the hydrogel composition. The co-monomers still remain as leachable monomers in the final hydrogel product. The free, leachable monomers may affect the properties of the film and the compatibility of the film with other materials. While co-monomers may be used in the present hydrogel film compositions, they are not required and, at the least, may be used in a reduced amount compared to conventional hydrogel compositions. In one embodiment, the monomer (c) is present in an amount of from about 0 to about 50 wt. % by weight of the composition, from about 0.5 to about 40 wt. %, from about 1 to about 30 wt. %, from about 2 to about 20 wt. %, even from about 5 to about 10 wt. % by weight of the composition.

Examples of suitable monomers (c) include, but are not limited to, organic silicone, or organo-modified silicone molecules with one polymerizable group. Non-limiting examples of suitable polymerizable groups include acrylate, methacrylate, vinyl, allyl, methallyl, acrylamides, methacrylamides, N-vinyl lactam, N-vinyl amide, olefinically unsaturated hydrocarbons with carboxylic acids or esters, etc. More specific polymerizable groups include, but are not limited to, N,N-dimethylacrylamide, N,N-dimethylmethacrylamide, N-hydroxyethyl acrylamide, N-vinyl-pyrrolidone, N-vinylpyrrole, N-vinyl succinimide, alkyl vinyl ethers, 2-acrylamido glycolic acid, 2-hydroxyethyl methacrylate (HEMA), 2-hydroxy ethylacrylate (HEA), hydroxypropyl methacrylate, dimethylaminoethyl methacrylate, glycerol methacrylate, 2-ethyl hexyl acrylate, butyl acrylate, isooctyl acrylate, methyl methacrylate, lauryl acrylate, dodecyl acrylate, butyl acrylate, acrylic acid, maleic anhydride, vinyl acetate, allyl alcohol, acrylic acid, methacrylic acid, vinyl acetate, N-vinyl caprolactum, N-vinylformamide, N-vinyl acetamide, N-vinyl-N-methyl acetamide, N, N-vinyl-3-methyl caprolactum, N-vinyl imidazole, 2-acrylamidoglycolic acid, N-hydroxyethyl acrylamide, N-tertbutyl acrylamide, N-isopropylacrylamide, N-isopropylmethacrylamide, 2-acrylamnido-2-methyl-1-propane sulfonic acid and its salts, (3-acrylamidopropyl)-trimethylammonium chloride, N,N-dimethylmethacrylamide, 3-acryloylamino-1-propanol, 2-acrylamidoglycolic acid, aminopropyl methacrylate, 3-tris(trimethylsiloxy) silylpropylmethacrylate (TRIS), bis-(trimethylsiloxy)methylsilylpropyl methacrylate, pentamethyldisiloxanepropylmethacrylate, pentamethyldisiloxanylmethylmethacrylate, (3-methacryloxy-2-hydroxypropyloxy)propylbis(trimethylsiloxy)silane (SIGMA), monomethacryloxypropyl terminated polydimethysiloxane, tris(trimethylsiloxy)silylpropyloxyethylmethacrylate, tris(trimethylsiloxy)silylpropyloxyethyl methacrylate, tris(trimethylsiloxy)silylpropyl methacryloxyethylcarbamate, tris(trimethylsiloxy)silylpropyl glycerol, N-[tris(trimethylsiloxy)silylpropyl] methacrylamide, pentamethyldisiloxanyl methyl methacrylate, phenyltetramethyl disiloxanyl ethyl ethacrylate, 3-[tris(trimethylsiloxy)silyl]propyl vinyl carbamate, 3-[tris(trimethylsiloxy)silyl]propyl vinyl carbonate, 2-(acryloxyethyoxy)trimethylsilane, N-(3-acryloxy-2-hydroxypropyl)-3-aminopropyl triethoxysilane, (acryloxymethyl)phenethyl trimethoxysilane, 3-(N-allylamino)propyltrimethoxysilane.

In one embodiment, the monomers (c) are selected from hydrophilic monomers such as N,N-dimethylacrylamide, N-vinyl-2-pyrrolidone, 2-hydroxyethyl methacrylate, 2-hydroxy ethylacrylate, dimethylaminoethyl methacrylate, etc.

The cross-linking agent (d) can generally have two or more reactive functional groups at different sites of the molecule. Typically, these sites contain polymerizable olefinic unsaturation groups. During curing, they form a covalent bond with two different polymer chains and form a stable three-dimensional network to improve the strength of these polymers. Non-limiting examples of suitable cross-linking agents include acrylates, methacrylates, acrylamide, methacrylamide, thio, cyanurate, etc. Few examples that can be used but not limited to are ethylene glycol dimethacrylate, 1,6-hexanediol diacrylate, ethylene glycol dimethacrylate, pentaerythritol tetramethacrylate, glycerol dimethacrylate, triallyl cyanurate, ethylenediamine dimethacrylamide, bisphenol A dimethacrylate, coatosil, diacrylate or dimethacrylate terminated polydisiloxanes, diacrylamide terminated polydimethyl siloxanes, dimethacrylamide terminated polydimethylsiloxanes, dimethacrylated polyether modified polydimethylsiloxanes, etc. Cross-linking agents conventionally used in contact lenses include ethylene glycol dimethacrylate, tetraethyleneglycol dimethacrylate and trimethyloylpropane trimethacrylate (about 0.1 to 2 wt. %). Other useful cross-linking agents include diethyleneglycol dimethacrylate, bisphenol A dimethacrylate, diglycidyl bisphenol A dimethacrylate, dimethacrylate-terminated polyethylene glycol, and reactive linear polyether modified silicones.

The polymers and hydrogel of this invention may also contain ultraviolet absorbents, pigments and colorants in the form of additives or co-monomers.

The present invention also provides silicone-hydrogel compositions comprising (meth)acrylate functionalized hydrophilic silicone monomer and conventional monomer such as HEMA or other contact lens monomers to produce soft, flexible water absorbing films. The polymers of the present invention can absorb about 10 wt. % to about 60 wt. % of water, showing excellent surface wettability and effective oxygen permeability, all of which are necessary for the better comfort when lens are worn and for good health of the human cornea. The present invention also provides contact lenses made from the silicone-hydrogel films of the claimed invention. These embodiments are further described below.

To form polymers or hydrogel composition of the present invention, the present polymers and optionally monomers are mixed and the resulting mixture is polymerized and cured to form transparent thin films by known thermal or UV cure techniques, using either peroxides or photo-initiators in the presence of cross-linking agents.

The pre-polymer compositions of the current invention may be used to form hydrophilic silicone homo/copolymers that produce silicone-hydrogel films having better oxygen permeability and significantly improved surface wettability in comparison to monomers with linear alkyl linking groups in the polyether chains. The contact lenses produced from the silicone-hydrogel films of the present invention do not require any expensive secondary treatments, like plasma oxidation or plasma coating, or internal wetting agents to improve wettability. That is, the contact lenses produced from silicone-hydrogel films of the present invention, without secondary treatment, are soft, flexible and inherently wettable and exhibit high oxygen permeability.

The polymers of the present invention form a clear, transparent homogeneous single-phase solution that can be either cured directly or with employing 0-50% 2-propanol or water or buffered solutions as additional homogenizing solvents, depending on the molecular weight of the present siloxane monomers, which are miscible with organic hydrophilic hydrogel monomers. Calculated solubility parameter values based on Fedors method (Robert F. Fedors, *Polymer Engineering and Science, February* 1974, vol. 14, No. 2) for the present inventive monomers range from approximately 16.5 to approximately 19 $(J/mol)^{1/2}$, which is closer to the solubility parameter value of conventional hydrogel monomers (such as HEMA, NVP and DMA) than silicone monomers such as TRIS. Miscibility is realized if the difference in solubility parameter between the instant inventive monomers and the hydrophilic co-monomers is less than about 7.7 $(J/mol)^{1/2}$.

In another embodiment of the present invention, the polymers may be formed into silicone-hydrogel films, via processes known in the art. The silicone-hydrogel films of the present invention are soft, flexible, and highly transparent. Silicone-hydrogel films made from the inventive polymers exhibit better surface wettability and oxygen permeability compared to films made using monomers having linear alkyl linked methacrylated silicone polyether chains. The oxygen permeability of the hydrogel films or lenses can be from 40 Dk to 400 Dk units by selecting the silicone pre-polymers, independently or in combinations, of the present invention. The present silicone hydrogel films were found to have dynamic advancing contact angles with water, in the range of 100° to 20° and absorb about 10 to 70 wt. % of water, which can vary depending on the molecular weight of the pre-polymers. The contact angle can also be altered in the defined range by adding wetting agents like poly(vinyl pyrrolidone), or poly(vinyl alcohol). The silicone hydrogels also have good mechanical properties (such as low modulus and high tear strength) required for the contact lens application.

Conventional silicone-hydrogel films are generally produced by curing a mixture of hydrophobic silicone monomers and hydrophilic hydrogel monomers in the presence of about 10 to 40 wt. % of an organic solvent, as they are incompatible with each other. However in the current invention, the inventive hydrophilic silicone macromers are found to be miscible with water or 2-propanol and hydrophilic hydrogel monomers (such as HEMA, NVP and DMA) and can form a homogeneous solution suitable to produce silicone-hydrogel films that are more commonly used in the contact lens manufacturing or miscible in "green solvents." The phrase "green solvents" can include, but is not limited to, water, buffers, inorganic salt solutions, multipurpose solutions, lens care solutions, a combination of two or more thereof, or a combination of any of these with solvents that are ophthalmic friendly.

In the present invention, the resulting polymers may be formed into silicone-hydrogel films via processes known in the art. Accordingly, the present invention is also directed to contact lens produced from either homo or copolymers of the present invention. The monomers/polymers of the present invention can be formed into contact lenses by spin casting processes, as disclosed in U.S. Pat. Nos. 3,408,429 and 3,496,254, cast molding processes, as disclosed in U.S. Pat. Nos. 4,084,459 and 4,197,266, combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates, tubes or rods, which may then be processed (e.g., cut or polished via. lathe or laser) to give a contact lens having a desired shape.

As stated above, the silicone-hydrogels of the present invention exhibit higher oxygen transport with improved surface wettable properties when compared to silicone-polyether copolymers having linear alkyl linking groups. The polymers employed in accordance with this invention are readily polymerized to form three-dimensional networks, which permit the transport of oxygen with improved wettability along with better mechanicals and optical clarity.

Specific use of the films include intraocular contact lenses, artificial corneas, and soft disposable long-wear contact lenses or as coatings for biomedical devices.

Additionally, the use of the present polymers allows for employing "green" extraction protocols to remove leachable molecules or monomers from the composition or the hydrogel product. As previously described, conventional hydrogel films for contact lenses employ a relatively large concentration of co-monomers (such as, for example, HEMA) and require treatment to extract the leachable monomers from the system. Extraction is typically carried out using organic solvents. The present polymers allow for significantly reducing, or eliminating, the additional co-monomer from the system. With the present polymer compositions, less harsh extraction protocols can be employed. In one embodiment, aqueous systems may be used for extraction including, but not limited to, water, organic or inorganic salt solutions, buffers, emulsions, commercial lens cleaning solutions, or any ophthalmically compatible solvent.

Apart from being suitable to form hydrogel compositions for use in making films for contact lens applications, the present compositions can also be used in a variety of applications. In one aspect the composition comprises homo or copolymers prepared in bulk or latex form. These homopolymer, copolymer, emulsion, and latex particles comprising the polymer of the current invention can be used as ingredients in personal care formulations including skin care, hair care, and nail care, such as lipsticks, mascaras, foundations, lotions, creams, shampoos, conditioners, and nail polishes, to improve their ware, tactile properties and ease of application. They also can be used in textile and fiber treatment applications to impart smooth, soft feel and wettability to both natural and synthetic fibers. Finally the homopolymer, copolymer, emulsion and latex particles can be incorporated into coating formulations for metal, plastic, wood and paper, such as varnishes, latex paints, and roofing compositions.

In one embodiment, the composition can be employed in a personal care composition as film formers. Examples of personal care compositions in which the composition can be utilized include, but are not limited to, deodorants, antiperspirants, antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-fizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin, combinations of two or more thereof, etc.

It will be appreciated that the compositions in which the compositions of the present inventions are employed may include other ingredients and components as desired for a particular purpose or intended use. For example, personal care compositions may include ingredients chosen from emollient, moisturizer, humectant, pigment, coated mica, colorant, fragrance, biocide, preservative, antioxidant, antimicrobial agent, anti-fungal agent, antiperspirant agent, exfoliant, hormone, enzyme, medicinal compound, vitamin, salt, electrolyte, alcohol, polyol, absorbing agent for ultraviolet radiation, botanical extract, surfactant, silicone oil, organic oil, wax, film former, thickening agent, particulate filler, clay, surfactants, emulsifiers, solvents, emollients, moisturizers, humectants, pigments, colorants, fragrances, biocides, preservatives, chelating agents, antioxidants, antimicrobial agents, anti-fungal agents, antiperspirant agents, exfoliants, hormones, enzymes, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, film formers, thickening agents, particulate fillers, silicones, clays, plasticizers, humectants, occlusive, sensory enhancers, esters, resins, film formers, film forming emulsifiers, high refractive index materials, combinations of two or more thereof, etc.

In another embodiment, the compositions may be utilized as film formers in an agricultural composition such as, for example, a fertilizer, a pesticide, etc.

In still another embodiment, the compositions can be employed in a component in adhesive formulations.

Aspects of the invention may be further understood with reference to the following non-limiting examples.

Aspects of the present invention may be further understood with reference to the following examples. The examples are for the purpose of illustrating aspects and embodiments of the present invention and are not necessarily intended to limit the scope of the appended claims.

EXAMPLES

Example 1: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide, and 2-hydroxyethyl methacrylate, with m:n:p=20:55:25, Mw~2600 g/mol, U=3

A round-bottom flask equipped with a stirring bar, a reflux condenser and a dropping funnel was charged with vinyl-cyclohexyl-epoxy functionalized trisiloxane (100 g) and toluene (100 mL), and the reaction mixture was heated to 70-75° C. At this point catalytic amount of titanium iso-propoxide (0.8 mol %) and TEMPO (2,2,6,6-Tetramethyl-piperidine 1-oxyl) (0.1 mmol) were added and the reaction mixture was further heated to 90° C. To this reaction mixture, acrylic acid (21 g) was added gradually over a period of 2 hours. After completion, the reaction mixture was stirred over Dowex-WBA resin (10 g) to remove unreacted acrylic acid. The product was decolorized using activated charcoal (1 wt. %) and filtered on a celite bed. The filtrate was distilled under vacuum to remove the organic solvents to yield a pale yellow color liquid, 5-(2-(1,1,1,3,5,5,5-heptamethyltrisiloxane-3-yl)ethyl)-2-hydroxycyclo-hexylacrylate.

Typically, polymerization was carried out in a round-bottom flask equipped with a stirring bar, a reflux condenser and a dropping funnel, which was charged with 25 g of -(2-(1,1,1,3,5,5,5-heptamethyltrisiloxane-3-yl)ethyl)-2-hy-droxycyclohexylacrylate, 16 g of N,N-Dimethyl acrylamide (DMA), 10 g of 2-Hydroxyethyl methacrylate (HEMA), and 75 mL of toluene. The reaction mixture was degassed using nitrogen in order to remove dissolved oxygen. 0.1 mole % of 1,1'-azobis(cyclohexanecarbonitrile) was used as a free radical source. 2-merceptoethenol (1.5 g) was added as a chain transfer agent under positive nitrogen flow. The reaction mixture was heated to 110-120° C. for ten hours. After completion of the polymerization the reaction mixture was distilled to remove organic solvents and to yield copolymer as a white free flowing powder. The powder obtained is hygroscopic in nature, hence, was stored under moist-free conditions. The reaction was monitored by $^1$H NMR spectroscopy and Gel permeation Chromatography.

The free hydroxyl ends of the copolymer were methacrylated further to get the ethylenically-unsaturated terminal group. A round bottom flask equipped with a dropping funnel and nitrogen inlet was charged with 50 g of copolymer, 100 g of toluene and 14 g of triethylamine, and the flask was placed in an ice-bath. To the reaction flask was added 12 g of methacryloyl chloride drop wise. The reaction was stirred at the same temperature for one hour and then warmed to room temperature (25° C.) for 12 hours. Triethylammonium hydrochloride salt formed during the reaction was filtered out using a funnel. The reaction mixture was distilled to remove organic solvents. The product was re-dissolved in 2-propanol and stirred on a Dowex WBA resin (10 g) to remove any methacrylic acid byproduct formed during the reaction. The copolymer solution was then decolorized using activated charcoal (1 wt. %). The charcoal dispersion was filtered on a Celite-S bed. 50 ppm Hydroquinone was added to the filtrate. Distillation of solvents yields pale yellow color functionalized copolymer as a solid. All the reaction steps and products were confirmed by $^1$H and $^{29}$Si NMR spectroscopy.

Example 2: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide, and 2-hydroxyethyl methacrylate, with m:n:p=15:60:25, Mw~4700 g/mol, U=3

Typically, polymerization was carried out in a round-bottom flask equipped with a stirring bar, a reflux condenser, and a dropping funnel. The flask was charged with 50 g of (2-(1,1,1,3,5,5,5-heptamethyltrisiloxane-3-yl)ethyl)-2-hydroxycyclohexylacrylate, 47 g of N,N-Dimethyl acrylamide (DMA), 26 g of 2-Hydroxyethyl methacrylate (HEMA), and 185 mL of toluene. The molar ratio of siloxane:Dimethylacrylamide:2-hydroxyethylmethacrylate was fixed to 15:60:25. The reaction mixture was degassed with nitrogen in order to remove dissolved oxygen. 0.1 mole % 1,1'-Azobis(cyclohexanecarbonitrile) was used as a free radical source. 2-Merceptoethenol (2 g) was added as a chain transfer agent under positive nitrogen flow. The reaction mixture was heated to 110-120° C. for ten hours. After completion of the polymerization the reaction mixture was distilled to remove organic solvents and to yield copolymer as a white free flowing powder. The powder obtained is hygroscopic in nature, and hence was stored under moist-free conditions. The reaction was monitored by $^1$H NMR spectroscopy and Gel permeation Chromatography.

The free hydroxyl ends of the copolymer were methacrylated further to get the ethylenically-unsaturated terminal group. A round bottom flask equipped with a dropping funnel and a nitrogen inlet was charged with 120 g of copolymer, 250 g of toluene, and 20 g of triethylamine. The flask was placed in an ice-bath. To the reaction mixture was added 17 g of methacryloyl chloride drop wise. The reaction was stirred at the same temperature for one hour and then warmed to room temperature (25° C.) for 12 hours. The triethylammonium hydrochloride salt formed was filtered using a funnel. The product was re-dissolved in 2-propanol and stirred on a Dowex WBA resin (10 g) to remove any methacrylic acid byproduct formed during the reaction. The copolymer solution was then decolorized using activated charcoal (1 wt. %). The charcoal dispersion was filtered on a Celite-S bed. 50 ppm Hydroquinone was added to the filtrate. Distillation of solvents yields a pale yellow color functionalized copolymer. All the reaction steps and products were confirmed by $^1$H and $^{29}$Si NMR spectroscopy.

Example 3: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide, and 2-hydroxyethyl methacrylate, with m:n:p=15:60:25, Mw~4700 g/mol, U=2

The free hydroxyl groups, of the copolymer of example 2, were methacrylated further to get the ethylenically-unsaturated terminal group. A round bottom flask equipped with a dropping funnel and a nitrogen inlet was charged with 30 g of copolymer, 100 g of toluene and 3 g of triethylamine. The flask was placed in an ice-bath. To the reaction mixture 2.8 g of methacryloyl chloride was added drop wise. The reaction was stirred at same temperature for one hour and then warmed to room temperature (25° C.) for 12 hours. The triethylammonium hydrochloride salt formed was filtered using a funnel. The reaction mixture was distilled to remove organic solvents. The product was re-dissolved in 2-propanol and stirred on a Dowex WBA resin (10 g) to remove any methacrylic acid byproduct formed during the reaction. The copolymer solution was then decolorized using activated charcoal (1 wt. %). The charcoal dispersion was filtered on a Celite-S bed. 50 ppm hydroquinone was added to the filtrate. Distillation of solvents yields a pale yellow color functionalized copolymer. All the reaction steps and products were confirmed by $^1$H and $^{29}$Si NMR spectroscopy.

Example 4: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide and 2-hydroxyethyl methacrylate, with m:n:p=15:60:25, Mw~2400 g/mol, U=3

Typically, polymerization was carried out in a round-bottom flask equipped with a stirring bar, a reflux condenser and a dropping funnel. The flask was charged with 25 g of -(2-(1,1,1,3,5,5,5-heptamethyltrisiloxane-3-yl)ethyl)-2-hydroxycyclohexylacrylate, 24 g of N,N-dimethyl acrylamide (DMA), 13 g of 2-hydroxyethyl methacrylate (HEMA) and 90 mL of 2-propanol. The molar ratio of siloxane:dimethylacrylamide:2-hydroxyethylmethacrylate was fixed to 15:60:25. The reaction mixture was degassed with nitrogen in order to remove dissolved oxygen. 0.1 mole % 1,1'-Azobis(cyclohexanecarbonitrile) was used as a free radical source. 2-merceptoethenol (2 g) was added as a chain transfer agent under positive nitrogen flow. The reaction mixture was heated to 90-95° C. for ten hours. After completion of the polymerization the reaction mixture was distilled to remove organic solvents and to yield copolymer as a white free flowing powder. The powder obtained is hygroscopic in nature, and hence was stored under moist-free conditions. The reaction was monitored $^1$H NMR spectroscopy and Gel permeation Chromatography.

The free hydroxyl ends of the copolymer were methacrylated further to get the ethylenically-unsaturated terminal group. A round bottom flask equipped with a dropping funnel and a nitrogen inlet was charged with 40 g of copolymer, 120 g of Methylethyl ketone and 9 g of triethylamine. The flask was placed in an ice-bath. To the reaction mixture was added 8 g of methacryloyl chloride drop wise. The reaction was stirred at the same temperature for one hour and then warmed to room temperature (25° C.) for 12 hours. The triethylammonium hydrochloride salt formed was filtered using a funnel. The product was re-dissolved in 2-propanol and stirred on a Dowex WBA resin (10 g) to remove any methacrylic acid byproduct formed during the reaction. The copolymer solution was then decolorized using activated charcoal (1 wt. %). The charcoal dispersion was filtered on a Celite-S bed. 50 ppm Hydroquinone was added to the filtrate. Distillation of solvents yields a pale yellow color functionalized copolymer. All the reaction steps and products were confirmed by $^1$H and $^{29}$Si NMR spectroscopy.

Example 5: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide, and 2-hydroxyethyl acrylate, with m:n: p=20:30:50, Mw~5200 g/mol, U=3

Typically, polymerization was carried out in a round-bottom flask equipped with a stirring bar, a reflux condenser, and a dropping funnel. The flask was charged with 25 g of -(2-(1,1,1,3,5,5,5-heptamethyltrisiloxane-3-yl)ethyl)-2-hydroxycyclohexylacrylate, 9 g of N,N-Dimethyl acrylamide (DMA), 17 g of 2-Hydroxyethyl acrylate (HEA), and 75 mL of 2-propanol. The molar ratio of siloxane:dimethylacrylamide:2-hydroxyethylacrylate was fixed to 20:30:50. The reaction mixture was degassed with nitrogen in order to remove dissolved oxygen. 0.1 mole % 1,1'-Azobis(cyclohexanecarbonitrile) was used as a free radical source. 2-Merceptoethanol (0.8 g) was added as a chain transfer agent under positive nitrogen flow. The reaction mixture was heated to 90-95° C. for ten hours. After completion of the polymerization, the reaction mixture was distilled to remove organic solvents and to yield a copolymer as a white free flowing powder. The powder obtained is hygroscopic in nature and was stored under moist-free conditions. The reaction was monitored $^1$H NMR spectroscopy and Gel permeation Chromatography.

The free hydroxyl ends of the copolymer were methacrylated further to get the ethylenically-unsaturated terminal group. A round bottom flask equipped with a dropping funnel and a nitrogen inlet was charged with 50 g of copolymer, 100 g of methylethyl ketone, and 11 g of triethylamine. The flask was placed in an ice-bath. To the reaction mixture was added 9 g of methacryloyl chloride drop wise. The reaction was stirred at the same temperature for one hour and then warmed to room temperature (25° C.) for 12 hours. The triethylammonium hydrochloride salt formed was filtered using a funnel. The product was re-dissolved in 2-propanol and stirred on a Dowex WBA resin (10 g) to remove any methacrylic acid byproduct formed during the reaction. The copolymer solution was then decolorized using activated charcoal (1 wt. %). The charcoal dispersion was filtered on a Celite-S bed. 50 ppm of Hydroquinone was added to the filtrate. Distillation of solvents yields a pale yellow color functionalized copolymer. All the reaction steps and products were confirmed by $^1$H and $^{29}$Si NMR spectroscopy.

Example 6: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide and Glycidyl methacrylate, with m:n: p=15:72:13, Mw~4700 g/mol, U=3

Typically, polymerization was carried out in a round-bottom flask equipped with a stirring bar, a reflux condenser and a dropping funnel. The flask was charged with 20 g of -(2-(1,1,1,3,5,5,5-heptamethyltrisiloxane-3-yl)ethyl)-2-hydroxycyclohexylacrylate, 23 g of N,N-Dimethyl acrylamide (DMA), 6 g of Glycidyl methacrylate (GMA), and 75 mL of 2-propanol. The molar ratio of siloxane:dimethylacrylamide:Glycidyl methacrylate was fixed to 15:72:13. The reaction mixture was degassed with nitrogen in order to remove dissolved oxygen. 0.1 mole % 1,1'-azobisisobutylonitrile was used as a free radical source. 2-Merceptoethenol (0.8 g) was added as a chain transfer agent under positive nitrogen flow. The reaction mixture was heated to 65-70° C. for ten hours. After completion of the polymerization the reaction mixture was distilled to remove organic solvents and to yield copolymer as a white free flowing powder. The powder obtained is hygroscopic in nature and was stored under moist-free conditions. The reaction was monitored $^1$H NMR, $^{13}$C NMR spectroscopy and Gel permeation Chromatography The free epoxy ends of the copolymer were acrylated further to get the ethylenically-unsaturated terminal group. A round bottom flask equipped with nitrogen inlet was charged with 45 g of copolymer, 100 g of 2-propanol, 1.5 g of Triethylamine and 5 g of Acrylic acid. 15 mg of Butylated hydroxytoluene was added as polymerization inhibitor to avoid any gelation. The reaction was stirred at 90-95° C. for 12 hours. After completion of reaction, the reaction mixture was stirred over Dowex WBA resin (10 g) to remove any acrylic acid byproduct formed during the reaction. Distillation of solvents yields white colored functionalized copolymer. All the reaction steps and products were confirmed by $^1$H, $^{13}$C and $^{29}$Si NMR spectroscopy.

Example 7: Synthesis of triblock copolymer of 5-(2-(1,1,1,3,5,5,5-heptamethyltrisiloxane-3-yl) ethyl)-2-hydroxycyclohexylacrylate, N-Vinylpyrrolidone, and 2-hydroxyethyl methacrylate, with m:n: p=55:36:9, Mw~4300 g/mol, U=2

Typically, polymerization was carried out in a round-bottom flask equipped with a stirring bar, a reflux condenser and a dropping funnel. The flask was charged with 30 g of -(2-(1,1,1,3,5,5,5-heptamethyltrisiloxane-3-yl)ethyl)-2-hydroxycyclohexylacrylate and 60 ml of Toluene. The reaction mixture was degassed with nitrogen in order to remove dissolved oxygen. 0.1 mole % 1,1'-azobis(cyclohexanecarbonitrile) was used as a free radical source. 2-merceptoethenol (0.7 g) was added as a chain transfer agent under positive nitrogen flow. The reaction mixture was heated to 110-120° C. After 15 minutes, 5 g of N-vinylpyrrolidone (NVP) and 5 ml of Toluene was added to reaction mixture drop wise over a period of two hours. This was followed by drop wise addition of 1.6 g of 2-Hydroxyethyl methacrylate (HEMA) and 5 mL of toluene. The reaction was continued for 8 hrs. After completion of the polymerization, the reaction mixture was precipitated in water to yield a copolymer as a white free flowing powder. The powder obtained is hygroscopic in nature and was stored under moist-free conditions. The reaction was monitored by $^1$H NMR spectroscopy.

The free hydroxyl ends of the copolymer were methacrylated further to get the ethylenically-unsaturated terminal group. A round bottom flask equipped with a dropping funnel and a nitrogen inlet was charged with 24 g of copolymer, 50 g of toluene, and 5 g of triethylamine. The flask was placed in an ice-bath. To the reaction mixture was added 4.5 g of methacryloyl chloride drop wise. The reaction was stirred at the same temperature for one hour and then warmed to room temperature (25° C.) for 12 hours. The triethylammonium hydrochloride salt formed was filtered using a funnel. The product was re-dissolved in 2-propanol and stirred on a Dowex WBA resin (10 g) to remove any methacrylic acid byproduct formed during the reaction. The copolymer solution was then decolorized using activated charcoal (1 wt. %). The charcoal dispersion was filtered on a Celite-S bed. 50 ppm hydroquinone was added to the filtrate. Distillation of solvents yields a pale yellow color functionalized copolymer. All the reaction steps and products were confirmed by $^1$H and $^{29}$Si NMR spectroscopy.

Example 8: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide, and Glycidyl methacrylate, with m:n: p=30:57:13, Mw~6000 g/mol, U=3

Typically, polymerization was carried out in a round-bottom flask equipped with a stirring bar, a reflux condenser and a dropping funnel. The flask was charged with 30 g of -(2-(1,1,1,3,5,5,5-heptamethyltrisiloxane-3-yl)ethyl)-2-hydroxycyclohexylacrylate, 13 g of N,N-Dimethyl acrylamide (DMA), 4 g of Glycidyl methacrylate (GMA), and 75 mL of 2-propanol. The molar ratio of siloxane:dimethylacrylamide:Glycidyl methacrylate was fixed to 30:57:13. The reaction mixture was degassed with nitrogen in order to remove dissolved oxygen. 0.1 mole % 1,1'-azobisisobutylonitrile was used as a free radical source. 2-merceptoethenol (0.6 g) was added as a chain transfer agent under positive nitrogen flow. The reaction mixture was heated to 65-70° C. for ten hours. After completion of the polymerization, the reaction mixture was distilled to remove organic solvents and to yield copolymer as a white free flowing powder. The powder obtained is hygroscopic in nature and was stored under moist-free conditions. The reaction was monitored by $^1$H NMR, $^{13}$C NMR spectroscopy, and Gel permeation Chromatography.

The free epoxy ends of the copolymer were acrylated further to get the ethylenically-unsaturated terminal group. A round bottom flask equipped with nitrogen inlet was charged with 45 g of copolymer, 100 g of 2-propanol, 1.5 g of triethylamine and 4 of acrylic acid. 14 mg of butylated hydroxytoluene was added as polymerization inhibitor to avoid any gelation. The reaction was stirred at 90-95° C. for 12 hours. After completion of reaction, the reaction mixture was stirred over Dowex WBA resin (10 g) to remove any acrylic acid byproduct formed during the reaction. Distillation of solvents yields white colored functionalized copolymer. All the reaction steps and products were confirmed by $^1$H, $^{13}$C, and $^{29}$Si NMR spectroscopy.

Example 9: Synthesis of Triblock Copolymer of (3-methacryloxy-2-hydroxypropyloxy)propylbis (trimethylsiloxy)silane (SIGMA), N,N-Dimethyl acrylamide, and Glycidyl methacrylate, with m:n:p=30:57:13, Mw~6100 g/mol Typically, polymerization was carried out in a round-bottom flask equipped with a stirring bar, a reflux condenser and a dropping funnel. The flask was charged with 10 g of (3-methacryloxy-2-hydroxypropyloxy)propylbis(trimethylsiloxy)silane (SIGMA), 4.5 g of N,N-Dimethyl acrylamide (DMA), 1.5 g of Glycidyl methacrylate (GMA), and 25 mL of 2-propanol. The molar ratio of siloxane:dimethylacrylamide:Glycidyl methacrylate was fixed to 30:57:13. The reaction mixture was degassed with nitrogen in order to remove dissolved oxygen. 0.1 mole % Vazo 88 was used as a free radical source. 2-mercaptoethenol (0.2 g) was added as a chain transfer agent under positive nitrogen flow. The reaction mixture was heated to 85-90° C. for 15 hours. After completion of the polymerization, the reaction mixture was distilled to remove organic solvents and to yield copolymer as a white solid. The solid obtained is hygroscopic in nature and was stored under moist-free conditions. The reaction was monitored by $^1$H NMR, $^{13}$C NMR spectroscopy, and Gel permeation Chromatography.

Example 10: Synthesis of Triblock Copolymer of Methacrylisobutyl Polyhedral Oligomeric Silsesquioxanes (POSS), N,N-Dimethyl Acrylamide, and Glycidyl Methacrylate, with m:n:p=30:57:13, Mw~10,000 g/mol Typically, polymerization was carried out in a round-bottom flask equipped with a stirring bar, a reflux condenser and a dropping funnel. The flask was charged with 10 g of Methacrylisobutyl Polyhedral Oligomeric Silsesquioxanes, 2 g of N,N-Dimethyl acrylamide (DMA), 0.6 g of Glycidyl methacrylate (GMA), and 25 mL of 2-propanol. The molar ratio of siloxane:dimethylacrylamide:Glycidyl methacrylate was fixed to 30:57:13. The reaction mixture was degassed with nitrogen in order to remove dissolved oxygen. 0.1 mole % Vazo 88 was used as a free radical source. 2-mercaptoethenol (0.1 g) was added as a chain transfer agent under positive nitrogen flow. The reaction mixture was heated to 85-90° C. for 15 hours. After completion of the polymerization, the reaction mixture was distilled to remove organic solvents and to yield copolymer as a straw yellow viscous liquid. The solid obtained is hygroscopic in nature and was stored under moist-free conditions. The reaction was monitored by $^1$H NMR, $^{13}$C NMR spectroscopy, and Gel permeation Chromatography Example 11: Synthesis of Triblock Copolymer of Methacrylate Polyethylene Glycol Functionalized Trisiloxane, N,N-Dimethyl Acrylamide, and Glycidyl Methacrylate, with m:n:p=30:57:13, Mw~9500 g/mol Typically, polymerization was carried out in a round-bottom flask equipped with a stirring bar, a reflux condenser and a dropping funnel. The flask was charged with 10 g of Methacrylate polyethylene glycol functionalized trisiloxane, 2.5 g of N,N-Dimethyl acrylamide (DMA), 0.8 g of Glycidyl methacrylate (GMA), and 25 mL of 2-propanol. The molar ratio of siloxane:dimethylacrylamide:Glycidyl methacrylate was fixed to 30:57:13. The reaction mixture was degassed with nitrogen in order to remove dissolved oxygen. 0.1 mole % Vazo 88 was used as a free radical source. 2-mercaptoethenol (0.1 g) was added as a chain transfer agent under positive nitrogen flow. The reaction mixture was heated to 85-90° C. for 15 hours. After completion of the polymerization, the reaction mixture was distilled to remove organic solvents and to yield copolymer as a white solid. The powder obtained is hygroscopic in nature and was stored under moist-free conditions. The reaction was monitored by $^1$H NMR, $^{13}$C NMR spectroscopy, and Gel permeation Chromatography Example 12: Synthesis of triblock copolymer of 3-[Tris(trimethylsiloxy)silyl]-propylmethacrylate (TRIS), N,N-Dimethyl acrylamide, and Glycidyl methacrylate, with m:n:p=30:57:13, Mw~6100 g/mol Typically, polymerization was carried out in a round-bottom flask equipped with a stirring bar, a reflux condenser and a dropping funnel. The flask was charged with 10 g of 3-[Tris(trimethylsiloxy)silyl]-propylmethacrylate, 4.5 g of N,N-Dimethyl acrylamide (DMA), 1.5 g of Glycidyl methacrylate (GMA), and 25 mL of 2-propanol. The molar ratio of siloxane:dimethylacrylamide:Glycidyl methacrylate was fixed to 30:57:13. The reaction mixture was degassed with nitrogen in order to remove dissolved oxygen. 0.1 mole % Vazo 88 was used as a free radical source. 2-mercaptoethenol (0.2 g) was added as a chain transfer agent under positive nitrogen flow. The reaction mixture was heated to 85-90° C. for 15 hours. After completion of the polymerization, the reaction mixture was distilled to remove organic solvents and to yield copolymer as a white solid. The solid obtained is hygroscopic in nature and was stored under moist-free conditions. The reaction was monitored by $^1$H NMR, $^{13}$C NMR spectroscopy, and Gel permeation Chromatography.

Example 13: Synthesis of triblock copolymer of 5-(2-(1,1,1,3,5,5,5-heptamethyltrisiloxane-3-yl) ethyl)-2-hydroxycyclohexylacrylate, N,N-Dimethyl acrylamide, and Glycidyl methacrylate, with m:n: p=30:57:13, Mw~6000 g/mol Typically, polymerization was carried out in a round-bottom flask equipped with a stirring bar, a reflux condenser and a dropping funnel. The flask was charged with 10 g of -(2-(1,1,1,3,5,5,5-heptamethyltrisiloxane-3-yl)ethyl)-2-hydroxycyclohexylacrylate, 4.5 g of N,N-Dimethyl acrylamide (DMA), 1.5 g of Glycidyl methacrylate (GMA), and 25 mL of 2-propanol. The molar ratio of siloxane:dimethylacrylamide:Glycidyl methacrylate was fixed to 30:57:13. The reaction mixture was degassed with nitrogen in order to remove dissolved oxygen. 0.1 mole % 1,1'-azobisisobutylonitrile was used as a free radical source. L-cysteine (0.3 g) was added as a chain transfer agent under positive nitrogen flow. The reaction mixture was heated to 75-80° C. for ten hours. After completion of the polymerization, the reaction mixture was distilled to remove organic solvents and to yield copolymer as a white free flowing powder. The powder obtained is hygroscopic in nature and was stored under moist-free conditions. The reaction was monitored by $^1$H NMR, $^{13}$C NMR spectroscopy, and Gel permeation Chromatography.

Examples of Hydrogel Films

Selected hydrogel films were prepared using 50-70 wt. % of copolymers described in above examples in a 2-proponal solution. The films were cured using 2-hydroxy-2-methyl propiophenone as a radical initiator (0.5 wt. %). The resultant clear, homogeneous solution was poured into PET (poly(ethylene terephthalate)) to a measuring gap of 1 mm. The formulations were cured by exposure to UV irradiation of 35 mW/cm$^2$ for 30-120 seconds. The films were evaluated for equilibrium water content, water wettability, oxygen permeability, and the modulus as listed in table 1.

The current invention provides reactive linear organosiloxane pre-polymers that can be used as a single component curable composition or in combination with other organic monomers. These pre-polymers allow for the opportunity to tune the structures to control hydrophilicity and/or oxygen permeability by the selection of silicone/organic units. This approach brings in better reproducibility and increased purity of the end products. The pre-polymers described in the present invention also provide hydrogels to make medical devices with reduced unreacted monomers or oligomers termed as leachables that are toxic to human health, thereby reduce the processing cost.

While the invention has been described with reference to various embodiments, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

What is claimed is:

1. A hydrophilic siloxane copolymer of the formula (1):

  (1)

wherein A and B are different, l is 1, m and n of formula (1) are independently 1-200, and 2<l+p<200;

W is a moiety having the general formula (2):

  (2)

wherein E is a divalent moiety chosen from a substituted, un-substituted, aliphatic, aromatic, cyclic, or acyclic hydrocarbon radical having 1-20 carbon atoms, optionally containing sulfur or oxygen; D is a monovalent hydrocarbon radical with 1-10 carbon atoms with a functional group independently selected from a

TABLE 1

|  | Film 1 | Film 2 | Film 3 | Film 4 | Film 5 | Film 6 | Film 7 | Film 8 | Film 9 | Film 10 | Film 11 |
| --- | --- | --- | --- | --- | --- | --- | --- | --- | --- | --- | --- |
| Example 1 (wt. %) | 50 | | | | | | | | | | |
| Example 2 (wt. %) | | 50 | 50 | 70 | | | | | | | |
| Example 3 (wt. %) | | | | | 70 | 70 | | | | | |
| Example 5 (wt. %) | | | | | | | 70 | | | | |
| Example 6 (wt. %) | | | | | | | | 50 | 50 | | |
| Example 8 (wt. %) | | | | | | | | | | 50 | |
| Example 8 (wt. %) | | | | | | | | | | | 80 |
| 2-Propanol (wt. %) | 50 | 50 | 50 | 30 | 30 | 30 | 30 | 50 | 50 | 50 | 20 |
| 2-Hydroxy-2-methyl propiophenone (% ge of Total) | 0.5 | 0.5 | 0.5 | 0.5 | 0.5 | 0.5 | 0.5 | 0.5 | 0.5 | 0.5 | 1.0 |
| Ethylene glycol dimethacrylate(% ge of Total) | | | | | 0.5 | 0.5 | | 0.5 | | 0.5 | 1.0 |
| Trimethylol propene triacrylate(% ge of Total) | | | | | | | 2.5 | | | | |
| Curing time (sec) | 60 | 60 | 80 | 30 | 30 | 60 | 80 | 120 | 120 | 120 | 270 |
| Physical appearance | Brittle | Self Standing | Self Standing | Brittle | Self Standing | Self Standing | Brittle | Self Standing | Self Standing | Self Standing | Self Standing |
| Optical appearance | Clear | Clear | Clear | Clear | Clear | Clear | Clear | Clear | Clear | Clear | Clear |
| H$_2$O uptake (% ge) | 20 | 42 | 38 | 35 | 42 | 44 | 35 | 64 | 65 | 63 | 70 |
| Modulus (Mpa) | NA | 2.5 ± 0.2 | 2.9 ± 0.2 | 3 ± 0.5 | 2 ± 0.2 | 1.2 ± 0.2 | 3 ± 0.5 | 0.5 ± 0.1 | 0.6 ± 0.2 | 0.8 ± 0.1 | 0.4 ± 0.1 | hydroxy, an ether, an ester, an amine, an amide, a carboxylic acid, or a combination of two or more thereof;

A is an organosilicone group-containing unit having the general formula (15):

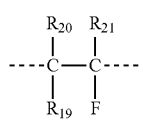

(15)

wherein $R_{19}$, $R_{20}$, and $R_{21}$ are selected from hydrogen or a monovalent hydrocarbon radical with 1 to 10 carbon atoms optionally containing a heteroatom; and F is expressed as having the general structure of formula (16):

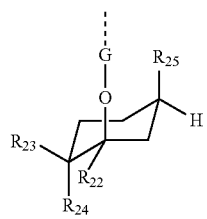

(16)

wherein $R_{22}$, $R_{24}$, and $R_{25}$ are independently chosen from hydrogen or a monovalent hydrocarbon radical with 1 to 5 carbon atoms optionally containing heteroatom; $R_{23}$ is chosen from a hydroxyl or an alkali metal salt thereof, an alkoxy, or a halogen; G is a divalent moiety independently chosen from a substituted or un-substituted, aliphatic or aromatic, cyclic or acyclic hydrocarbon radical having 1-20 carbon atoms optionally containing a heteroatom; H in formula (16) is defined by the general formula (17),

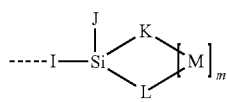

(17)

wherein I in formula (17) is an alkylene group with 1-16 carbon atoms; and
(i) when m in formula (17) is zero, M in formula (17) is not present and K is independently selected from:
  a) $CH_3$, $-O-[Si(CH_3)_2O]_n-Si(CH_3)_3$, $-OSi(CH_3)_3$;
  b)

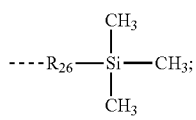

(18)

c)

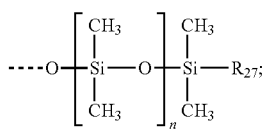

(19)

and d)

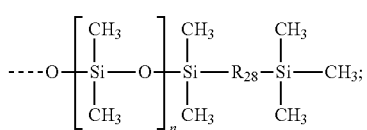

(20)

wherein $R_{26}$ and $R_{28}$ are a divalent hydrocarbon radicals with 1 to 5 carbon atoms, and $R_{27}$ is chosen from hydrogen or a monovalent hydrocarbon radical with 1 to 10 carbon atoms; wherein n in any in formulae (19) and (20) is an integer selected from 1-50;

and J and L are independently selected from $CH_3$, $-OSi(CH_3)_3$, or $-O-[Si(CH_3)_2O]n-Si(CH_3)_3$; or (ii) when m in formula (17) is greater than 0, J is $CH_3$, K is $+O-Si(CH_3)_2-$, L is $-OSi(CH_3)_2O$, and M is $-[OSi(CH_3)_2]_n-$, where n is an integer selected from 1-50;

B is a hydrophilic group-containing unit having the general formula (13)

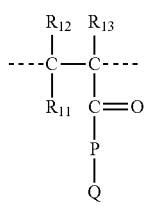

(13)

wherein P in formula (13) is selected from O or $NR_{14}$ wherein $R_{14}$ is a hydrogen or monovalent hydrocarbon radical with 1 to 5 carbon atoms optionally containing a heteroatom; $R_{11}$, $R_{12}$ and $R_{13}$ are independently selected from a hydrogen or monovalent hydrocarbon radical with 1 to 10 carbon atoms optionally containing a heteroatom; Q is a substituted or un-substituted, aliphatic, aromatic, cyclic, or acyclic hydrocarbon radical comprising of 1-50 carbon atoms, optionally containing a heteroatom, with a functional group independently selected from a hydroxyl, an ether, an ester, an amino, or a carboxylic acids; and C in formula (1) is an organic group-containing unit having the general formula (14):

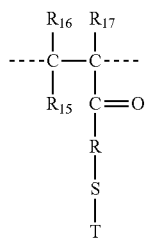

(14)

wherein $R_{15}$, $R_{16}$ and $R_{17}$ are independently selected from a hydrogen or monovalent hydrocarbon radical with 1-10 carbon atoms; R in formula (14) is selected from O or $NR_{18}$ wherein $R_{18}$ is hydrogen or a monovalent hydrocarbon radical with 1 to 5 carbon atoms optionally containing a heteroatom; S is a divalent hydrocarbon radical with 1-20 carbon atoms chosen from a substituted or un-substituted aliphatic, cyclic, or aromatic hydrocarbon, optionally containing a heteroatom; and T is a monovalent hydrocarbon radical with 1-10 carbon atoms with a functional moiety chosen from a hydroxyl, an epoxy, an ether, an ester, an amine, an amide, or a carboxylic acid.

2. The copolymer of claim 1 wherein H in formula (16) has a formula (17a):

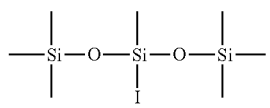

(17a)

wherein $R_{39}$ is a methyl group or —O—Si(CH$_3$)$_3$.

3. The copolymer of claim 1 wherein H in formula (16) has a formula (8a):

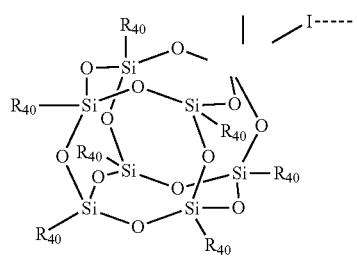

(8a)

wherein $R_{40}$ is a linear or branched monovalent hydrocarbon radical with 1-50 carbon atoms.

4. The copolymer of claim 1, wherein the ratio of m:n:p is from about 5-60:20-80:5-60, with the proviso that the total of the ratio adds up to 100.

5. A composition comprising a hydrophilic siloxane copolymer of the formula (1):

(1)

wherein A and B are different, l is 1, m and n in formula (1) are independently 1-200, and 2<l+p<200;
W is a moiety having the general formula (2):

(2)

wherein E is a divalent moiety chosen from substituted, un-substituted, aliphatic, aromatic, cyclic, or acyclic hydrocarbon radical having 1-20 carbon atoms, optionally containing sulfur or oxygen; D is a monovalent hydrocarbon radical with 1-10 carbon atoms with a functional group independently selected from a hydroxy, an ether, an ester, an amine, an amide, a carboxylic acid, or a combination of two or more thereof;

A is an organosilicone group-containing unit having the general formula (15):

(15)

wherein $R_{19}$, $R_{20}$, and $R_{21}$ are selected from hydrogen or a monovalent hydrocarbon radical with 1 to 10 carbon atoms optionally containing a heteroatom; and F is expressed as having the general structure of formula (16):

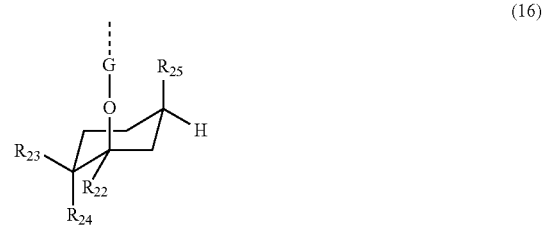

(16)

wherein $R_{22}$, $R_{24}$, and $R_{25}$ are independently chosen from hydrogen or a monovalent hydrocarbon radical with 1 to 5 carbon atoms optionally containing heteroatom; $R_{23}$ is chosen from a hydroxyl or an alkali metal salt thereof, an alkoxy, or a halogen; G is a divalent moiety independently chosen from a substituted or un-substituted, aliphatic or aromatic cyclic or acyclic hydrocarbon radical having 1-20 carbon atoms optionally containing a heteroatom; H in formula (16) is defined by the general formula (17),

(17)

wherein I in formula (17) is an alkylene group with 1-16 carbon atoms; and (i) when m in formula (17) is zero, M in formula (17) is not present and K is independently selected from:

a) CH$_3$, —O—[Si(CH$_3$)$_2$O]$_n$—Si(CH$_3$)$_3$, —OSi(CH$_3$)$_3$;

b)

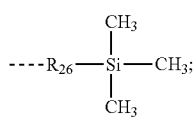
(18)

c)

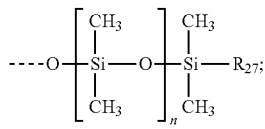
(19)

and d)

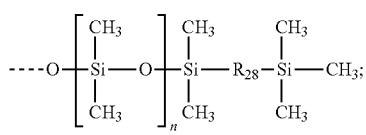
(20)

wherein $R_{26}$ and $R_{28}$ are divalent hydrocarbon radicals with 1 to 5 carbon atoms, and $R_{27}$ is chosen from hydrogen or a monovalent hydrocarbon radical with 1 to 10 carbon atoms; wherein n in any in formulae (19) and (20) is an integer selected from 1-50;

and J and L are independently selected from $CH_3$, $-OSi(CH_3)_3$, or $-O-[Si(CH_3)_2O]n-Si(CH_3)_3$; or (ii) when m in formula (17) is greater than 0, J is $CH_3$, K is $-O-Si(CH_3)_2-$, L is $-OSi(CH_3)_2O$, and M is $-[OSi(CH_3)_2]_n-$, where n is an integer selected from 1-50;

B is a hydrophilic group-containing unit having the general formula (13)

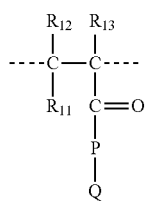
(13)

wherein P in formula (13) is selected from O or $NR_{14}$ wherein $R_{14}$ is a hydrogen or monovalent hydrocarbon radical with 1 to 5 carbon atoms optionally containing a heteroatom; $R_{11}$, $R_{12}$, and $R_{13}$ are independently selected from a hydrogen or monovalent hydrocarbon radical with 1 to 10 carbon atoms optionally containing a heteroatom; Q is a substituted or un-substituted, aliphatic, aromatic, cyclic, or acyclic hydrocarbon radical comprising of 1-50 carbon atoms, optionally containing a heteroatom, with a functional group independently selected from a hydroxyl, an ether, an ester, an amino, or a carboxylic acids; and C in formula (1) is an organic group-containing unit having the general formula (14):

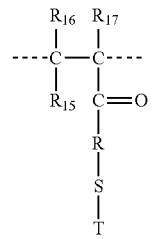
(14)

wherein $R_{15}$, $R_{16}$ and $R_{17}$ are independently selected from a hydrogen or monovalent hydrocarbon radical with 1-10 carbon atoms; R in formula (14) is selected from O or $NR_{18}$ wherein $R_{18}$ is hydrogen or a monovalent hydrocarbon radical with 1 to 5 carbon atoms optionally containing a heteroatom; S is a divalent hydrocarbon radical with 1-20 carbon atoms chosen from a substituted or un-substituted aliphatic, cyclic, or aromatic hydrocarbon, optionally containing a heteroatom; and T is a monovalent hydrocarbon radical with 1-10 carbon atoms with a functional moiety chosen from a hydroxyl, an epoxy, an ether, an ester, an amine, an amide, or a carboxylic acid; and wherein the composition is an emulsion, a latex, or a personal care composition.

6. The composition of claim 5 wherein H in formula (16) has a formula (17a):

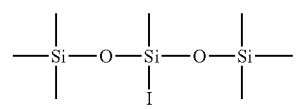
(17a)

wherein $R_{39}$ is a methyl group or $-O-Si(CH_3)_3$.

7. The composition of claim 5 wherein H in formula (16) has a formula (8a):

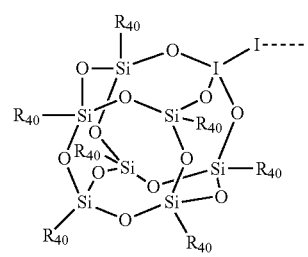
(8a)

wherein $R_{40}$ is a linear or branched monovalent hydrocarbon radical with 1-50 carbon atoms.

8. The composition of claim 5, wherein the ratio of m:n:p is from about 5-60:20-80:5-60, with the proviso that the total of the ratio adds up to 100.

9. The composition of claim 5, wherein the composition further comprises a cure initiator; optionally a monomer chosen from a vinylic monomer, an acrylamide monomer, an acrylic monomer, or a combination of two or more thereof; and optionally a cross-linker.

10. The composition of claim 9, wherein the vinylic monomer is chosen from N-vinyl-pyrrolidone (NVP), N-vinyl-caprolactam, N-vinyl-acetamide, N-vinyl-formamide and N-vinyl-isopropylamide, vinyl benzene, vinyl naphthalene, vinyl pyridine, vinyl alcohol, vinyl containing silicones, or a combination of two or more thereof; the acrylic monomers are chosen from 2-hydroxy-ethyl-methacrylate (HEMA), 2-hydroxy-ethyl-acrylate (HEA), hydroxyl propyl methacrylate, trimethylammonium 2-hydroxy propyl methacrylate hydrochloride, dimethylaminoethyl methacrylate, glycerol methacrylate, N,N-Dimethylacrylamide (DMA), N-isopropylacrylamide, acrylamide, methacrylamide, acrylic acid, methacrylic acid, any acrylated hydrophilic or hydrophobic organo-silicones present in the art, or combinations of two or more thereof.

11. The composition of claim 9, wherein the initiator is a thermal or a photo initiator chosen from 2,2'-azobis (2,4-dimethylpentanenitrile), 2,2'-azobis (2-methylpropanenitrile), 2,2'-azobis (2-methylbutanenitrile), peroxides such as benzoyl peroxide, benzoin methyl ether, diethoxyacetophenone, a benzoylphosphine oxide, 2-hydroxy-2-methyl propiophenone (HMPP), 1-hydroxycyclohexyl phenyl ketone and Darocur and Irgacure types.

12. The composition of claim 9, wherein the cross-linker is chosen from ethylene glycol dimethacrylate and trimethyloylpropane trimethacrylate, diethyleneglycol dimethacrylate, bisphenol A dimethacrylate, diglycidyl bisphenol A dimethacrylate and dimethacrylate-terminated polyethylene glycol and reactive linear polyether modified silicones.

13. The composition of claim 5, wherein the composition is a hydrogel.

14. A contact lens comprising the hydrogel of claim 13.

15. An article comprising a coating formed from the composition of claim 5, wherein the coating is disposed on at least a portion of a surface of the article.

16. A process for forming a contact lens comprising forming a film from the composition of claim 5 into a contact lens; and removing any leachable monomers from contact lens.

17. The process of claim 16, wherein removing the leachable monomers comprises treating the contact lens with an aqueous systems.

18. The process of claim 16 wherein the process comprises treating the contact lens with water, an organic salt solution, an inorganic salt solutions, a buffer, an emulsion, an ophthalmically compatible solvent in the temperature range of 20-125° C. for extraction, or a combination of two or more thereof.

* * * * *